Figure 1:
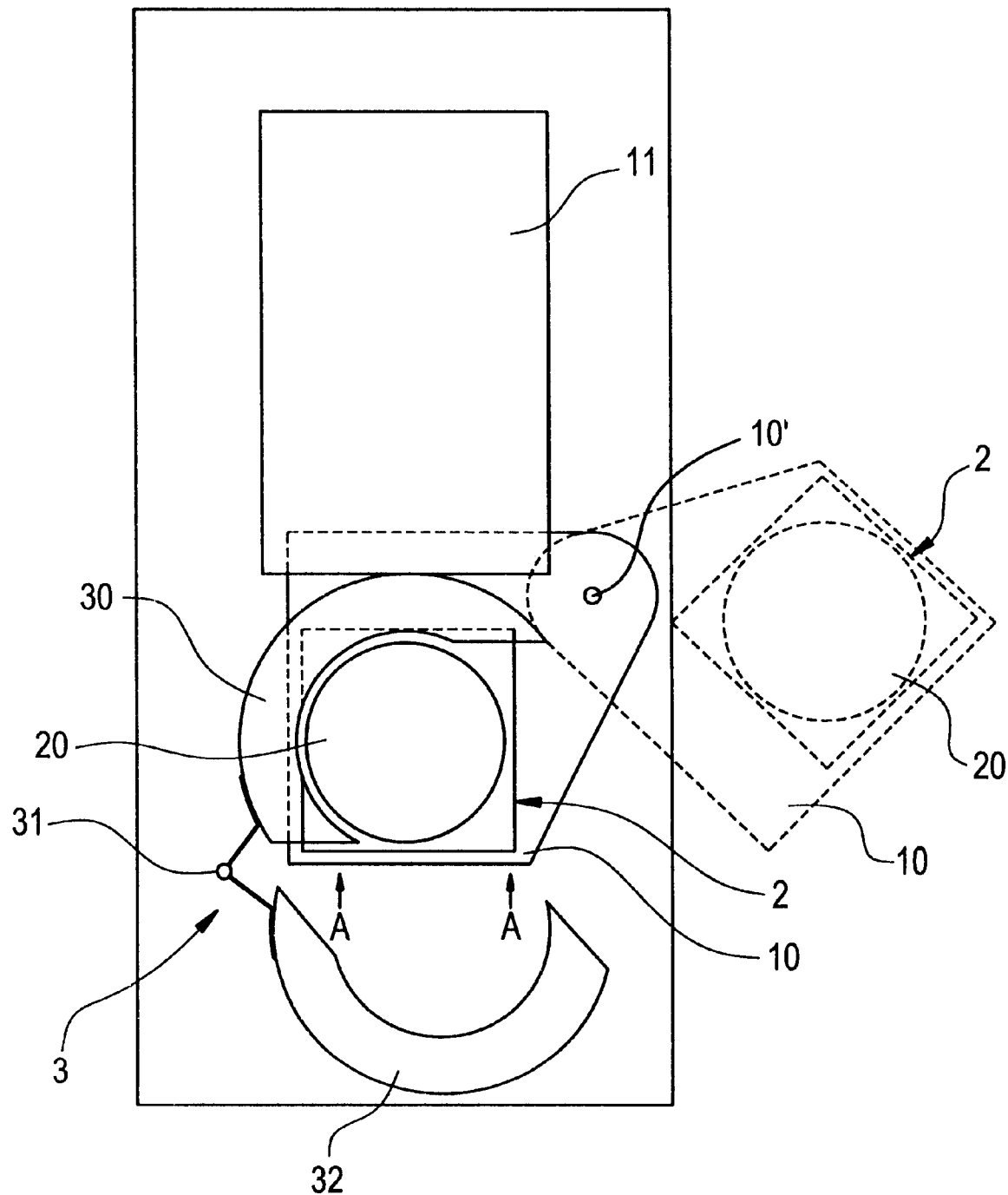

United States Patent
Rohe et al.

[19]

[11] Patent Number: 6,137,114
[45] Date of Patent: Oct. 24, 2000

[54] IRRADIATION APPARATUS

[75] Inventors: Karl-Heinz Rohe, Haan; Johann Kindlein, Oberhausen; Karl Weinlich, Wuppertal; Wolfgang Schreckenberg, Dusseldorf, all of Germany

[73] Assignees: Isotopen-Technik; Dr. Sauerwein GmbH, both of Haan, Germany

[21] Appl. No.: 08/983,051

[22] PCT Filed: Jul. 11, 1996

[86] PCT No.: PCT/EP96/03047

§ 371 Date: Mar. 26, 1998

§ 102(e) Date: Mar. 26, 1998

[87] PCT Pub. No.: WO97/03722

PCT Pub. Date: Feb. 6, 1997

[30] Foreign Application Priority Data

Jul. 15, 1995 [DE] Germany ............................ 195 25 811
May 24, 1996 [DE] Germany ........................ 296 09 310 U

[51] Int. Cl.[7] ................................ G21K 5/10; A61N 5/10
[52] U.S. Cl. ...................................... 250/497.1; 250/498.1
[58] Field of Search ............................. 250/497.1, 498.1; 600/3, 7

[56] References Cited

U.S. PATENT DOCUMENTS

| | | | |
|---|---|---|---|
| 3,669,093 | 6/1972 | Sauerwein et al. | 250/497.1 |
| 4,631,415 | 12/1986 | Sauerwein et al. | 250/497.1 |
| 4,851,694 | 7/1989 | Rague et al. | 250/497.1 |
| 5,139,473 | 8/1992 | Bradshaw et al. | 600/3 |

FOREIGN PATENT DOCUMENTS

| | | |
|---|---|---|
| 0 138 088 | 9/1984 | European Pat. Off. . |
| 0 278 829 | 1/1988 | European Pat. Off. . |
| 0 633 041 A1 | 11/1995 | European Pat. Off. . |
| 36 43 902 | 6/1988 | Germany . |

OTHER PUBLICATIONS

International Search Report dated Nov. 29, 1996.
International Preliminary Examination Report dated Sep. 30, 1997.

*Primary Examiner*—Jack Berman
*Attorney, Agent, or Firm*—Vickers, Daniels & Young

[57] ABSTRACT

An irradiation apparatus has at least one exchangeable radiation source that may be moved by means of a transport cable between at least one rest position and at least one irradiation position and a long-distance transport container for radiation sources to be exchanged. In order to reduce the danger of control errors, the rest position is located inside the long-distance transport container and the transport container forms or may form an integral part of the irradiation apparatus. For that purpose, interface elements are provided on the transport container and other parts of the irradiation apparatus. By winding and unwinding the transport cable on and from a feeding drum with a cable-receiving groove at least partially covered by a pressing strip, particularly thin transport cables may be used, so that the width of the pressing strip substantially corresponds to the width of the cable-receiving groove. The pressing strip is helically wound in the cable-receiving groove around the feeding drum, in the axial or radial direction with respect to the feeding drum, and the cable-receiving groove is thus covered in a substantially uninterrupted manner. Means for lifting, preferably also for deflecting and lowering again the pressing strip, may be moved along the transport cable in relation to the feeding drum in order to let free an output joint for the transport cable from the feeding drum.

35 Claims, 12 Drawing Sheets

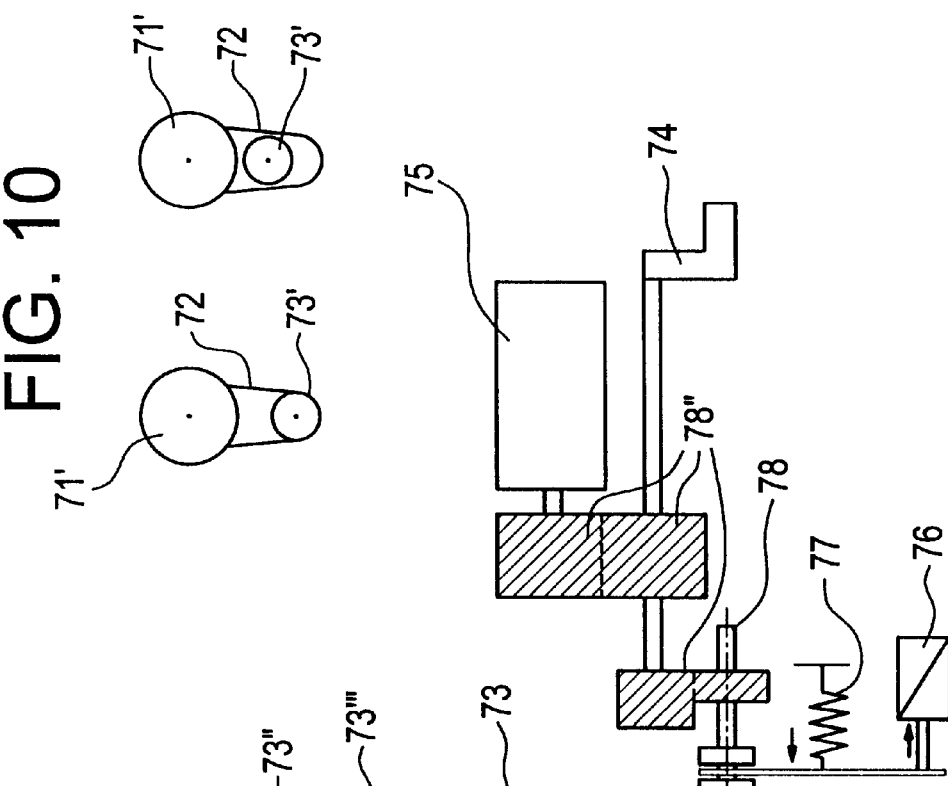
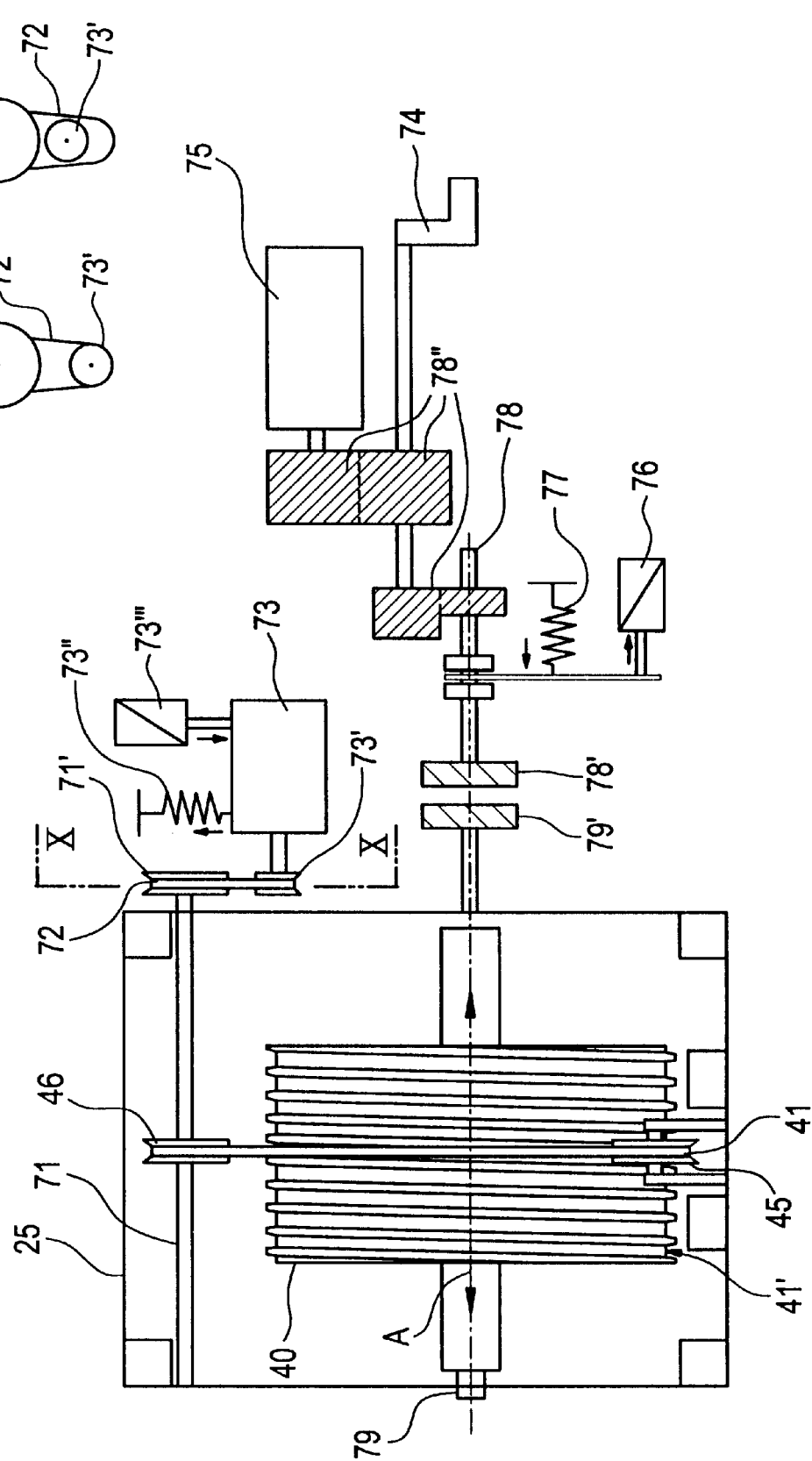

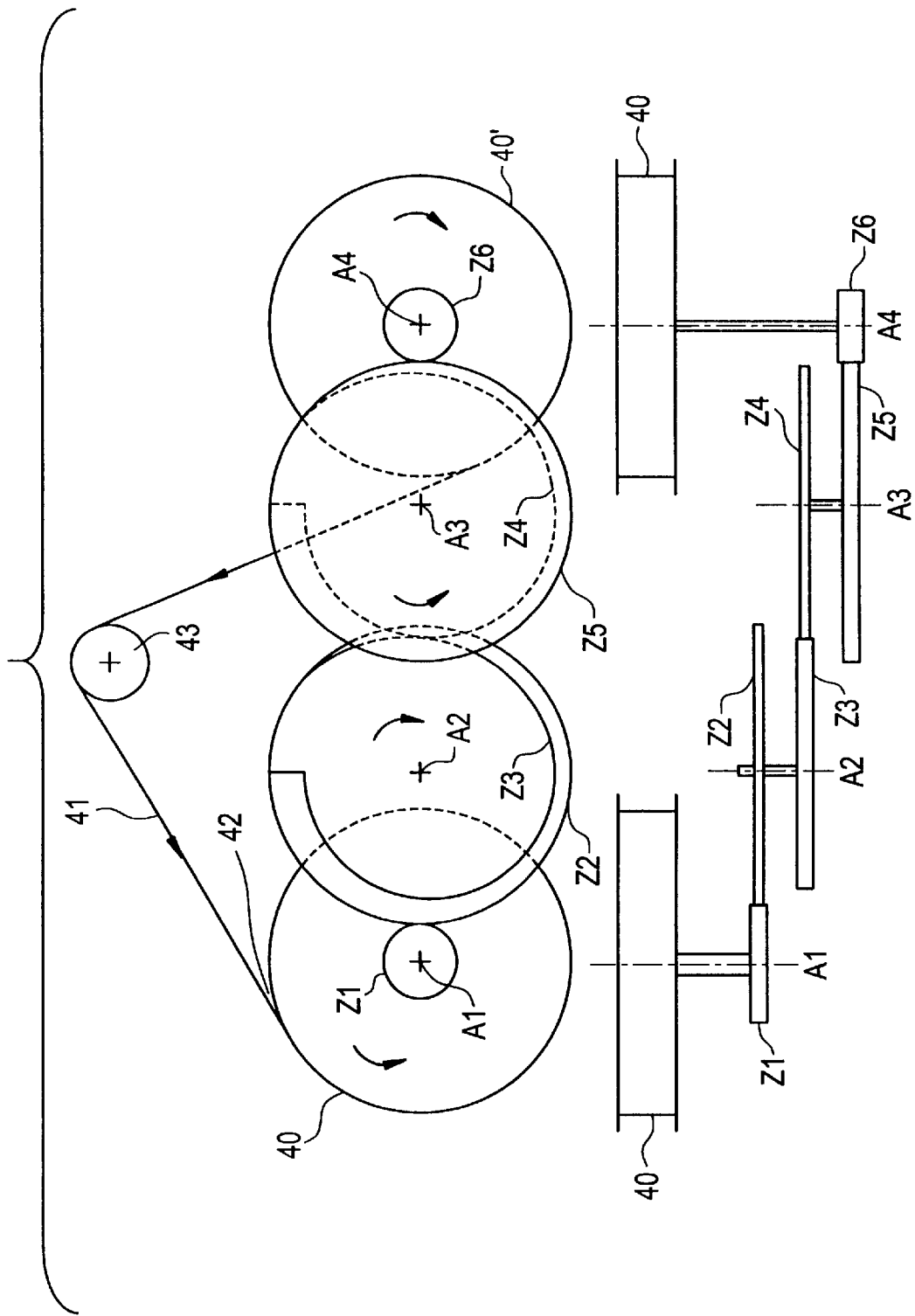

IRRADIATION APPARATUS

The invention relates to an irradiation apparatus having at least one exchangeable radiation source that can be moved between at least one non-operative position and at least one radiating position by means of a transport cable, the apparatus further having a transport container for transporting radiation sources to be exchanged.

An irradiation apparatus of this type is known from, for example, EP-B1-0 138 088, the content of which is incorporated by reference into the disclosure of the present description.

The object of this known irradiation apparatus, which includes a plurality of radiation sources, is to simultaneously insert a predeterminable number of radiator holding elements into the corresponding number of hollow probes by means of a single drive device. In one specific embodiment, the irradiation apparatus is equipped with only as many radiation sources as are necessary for the therapy to be performed in each treatment situation. For this purpose, the radiation sources are accommodated in small, easy-to-handle, flat cassettes that contain a radiation-source shield in addition to a drive-cable storage drum. The individual cassettes are manually inserted with their flat sides close together into an easily-accessible cassette compartment such that the cassette housing latches with the irradiation apparatus in a closely-adjacent arrangement. Therefore, for an individual radiation therapy, it is only necessary to click the correct cassette combination into the irradiation apparatus. This relieves the treatment technician of the task of transferring the radiator to be used from shielded storage containers into the irradiation apparatus and back as needed using the transport cable, as was formerly the case. Because the flat cassettes must be compact and must be able to be coupled among themselves in the irradiation apparatus, they are not readily suitable for long-distance transport, for example from and to the manufacturer/disposer. Hence, irradiation apparatuses of this type additionally necessitate a radiation-source transport container.

More stringent safety requirements are placed on generic irradiation apparatuses that are intended for use in intra-arterial irradiation to prevent a post-angioplasty restenosis. An irradiation apparatus of this type and a treatment method are described in, among other publications, EP-A1-0 633 041. This publication is incorporated by reference into the disclosure of the present patent application.

The known irradiation apparatuses are especially subject to a certain risk of operator's error during exchange of the radiation source, so that the radiation source can only be exchanged by specially trained personnel. The radiation sources are supplied to the user in a transport container that typically has two channels. The one channel serves to receive the old radiation sources, that is, the sources to be exchanged, while the other channel serves to receive the fresh radiation source. The irradiation apparatus is connected to the empty channel of the transport container by way of a transport hose. The transport cable subsequently moves the radiation source to be exchanged into the transport container. The drive-side end of the transport cable is detached by the drive after the radiator-side end has been secured against sliding in the transport container. The transport hose is subsequently connected to the channel containing the fresh radiation source, and the fresh radiation source is transferred into the irradiation apparatus in reverse order with respect to the old radiation source. The exchange of radiation sources is a critical situation, because the radiation source is forced to exit the shield of the irradiation apparatus via the transport hose during the process, and because the transport cable must be completely detached and recoupled. In particular, any arbitrary radiation source can be drawn into the irradiation apparatus, so confusion or errors can occur over the whereabouts of old or new radiation sources.

It is therefore the object of the invention to provide an irradiation apparatus in which the risk of an operator's error is reduced.

The solution is an irradiation apparatus having the features of claims 1, 3 and/or 4.

In irradiation apparatuses of the invention, the user stores the radiation source in a shield block when the source is in its position of non-use (non-operative position), and—as a standard practice—the source is moved into the radiating position by means of a transport cable. The shield surrounds the irradiation apparatus such that the transmitted radiation of the irradiation apparatus then meets the specifications for radiation-source containers regarding storage and use of the radiation sources. In accordance with the invention, the radiation-protection container (transport container) used for long-distance transport of the radiation source between the supplier and the user (client) serves as a component of the irradiation apparatus that is or can be integrated. It is therefore inserted much like a key (transport container) into a lock (remaining part of the irradiation apparatus), for which purpose corresponding interface means are provided. This feature creates a usable unit (irradiation apparatus) (claim 1). This prevents the radiation source from leaving its shield at the user's (client's) location during the exchange, for example, for a fresh radiation source. Furthermore, this feature can prevent confusion about used or fresh radiation sources remaining in the apparatus, because a radiation source is associated with exactly one long-distance transport container.

These properties of the apparatus are especially advantageous for the user in that he can work with sources of different specifications (with respect to activity, energy and geometry) without difficulty. Thus, it is readily possible to change from HDR to PDR (Pulse-Dose Rate) mode and to use a source that is optimally adapted to the application.

To avoid having to excessively increase the transport weight of a transport container of the invention, the transport container can include a shield that meets the specifications for long-distance radiation-source transport containers, and the remaining part of the irradiation apparatus can have a shield that surrounds at least parts of the transport container such that, with respect to the non-operative position of the irradiation apparatus, the transmitted radiation of the apparatus meets (more rigorous) specifications for radiation-source storage containers (claim 2). Of course, the shield of the long-distance transport container can meet the specifications for radiation-source storage containers in certain spatial directions, while it is not sufficiently strong in other spatial directions. This is a compromise between the transport, weight and the operator's comfort in inserting the transport container into the irradiation apparatus.

The design of an irradiation apparatus of the invention can be simplified if the transport container has a spiral-shaped transport channel that extends through, inside which the storage position is located. The transport cable can enter at one end of the transport channel, and be connected to an upstream drive, such as a storage drum. The transport cable pushes the radiation source from behind through the transport channel to transfer the source from its non-operative position into its radiating position.

The irradiation apparatus shield that surrounds the transport container in the operating position can include a shield hood, preferably one that swings open. This simplifies the exchange of radiation sources, and ensures that, after the transport container has been inserted into the irradiation apparatus, the entire shield meets the specifications for radiation-source storage containers.

As a further measure for avoiding operator's errors, means can be provided for automatically locking the radiation source or the transport cable in a transport position during transport of the transport container. This measure can prevent personnel from forgetting to lock the radiation source prior to transport. The radiation source or transport cable is preferably automatically locked when the transport container is removed from the irradiation apparatus.

A transport-cable storage element, preferably a storage drum, onto or from which the transport cable is wound and unwound, respectively, can be provided on the transport container. so the transport container and a transport-cable storage element, particularly a storage drum, are combined to form a transport module (claim 3). With this measure, the transport cable need not be separated from its drive unit for transporting the radiation source, a procedure during which a wide variety of errors, particularly operator's errors, could occur. Of course, the transport module can include further transport-cable drive means. It can be advantageous, however—especially with regard to weight—to provide transport-cable drive means, such as a mechanical drive, in the other part of the irradiation apparatus, which means are connected to the transport module or transport-cable storage element through suitable couplings when the transport module is inserted into the other part of the irradiation apparatus. Of course, this coupling can preferably be effected automatically. The modular unit comprising the transport container and the transport-cable storage element also has the advantage of increased precision in the determination of the radiator's position, because any manufacturing tolerances can be taken into account as unalterable correction values, for example.

To increase safety, the transport module can include means for locking the storage drum, preferably automatically, during transport of the transport module. This prevents an actuation of the transport-cable drive during transport of the radiation source.

The locking means are preferably enabled automatically prior to the initiation of movement of the radiation source from its non-operative position into the radiating position (claim 5). This prevents damage to the assemblies of the irradiation apparatus of the invention, including the transport container or transport module. The locking means are preferably enabled automatically upon the insertion of the transport module or transport container into the irradiation apparatus.

Extremely thin transport cables are required for gamma or beta radiation sources, particularly for irradiation in the vicinity of the heart.

Flexible sources having a highly flexible lead wire are advantageous in allowing radiation sources to be pushed through catheters having extremely small bending radii (FIG. 15).

To prevent the transport cable from collapsing, for example, a transport-cable drive is proposed, with which even extremely thin transport cables can be driven without collapsing or looping. In this instance, the transport cable is wound onto or unwound from a storage drum known per se and having a cable-receiving groove that is covered at least partially by a pressing band; a novel pressing band on the part of the transport cable that is wound in spiral fashion onto the storage drum is wound onto the storage drum, extensively parallel to the transport cable (claim 4). The pressing band is comparatively narrow; the extension of its width only covers one winding of the transport cable. Thus, the transport cable can be wound in spiral fashion, in the axial or radial direction, onto the storage drum. Consequently, the pressing band presses the transport cable until it occupies a very small region directly in front of the point from which the transport cable is lifted from the storage drum into the cable-receiving groove. In contrast to the pressing bands known from the prior art, in this case the entire length of the transport cable that is wound onto the storage drum is pressed onto the storage drum, that is, into the cable-receiving groove, with practically negligible interruptions. To ensure that the cable is also guided without collapsing or looping in the region around the lifting point of the transport cable from the storage drum, a pressing roller and/or a cable-guiding part with which the transport cable can be lifted from the storage drum can be provided in this region. Of course, a pressing-band guidance of this type can be employed advantageously, independently of the use of a cable-receiving groove. Thus, a transport-cable drive is created that can reliably drive extremely thin transport cables, for example those that are necessary for preventing post-angioplasty restenosis through intra-arterial irradiation.

In the region around the lifting point of the transport cable from the storage drum, the pressing band can be guided, for example by means of deflection rollers, around the storage drum in the opposite direction of the winding direction of the storage drum. This can prevent unnecessary crossings or deflections of the pressing band or the transport cable, and both the pressing band and the transport cable are extensively guided in a plane extending perpendicular to the shaft of the storage drum.

For gentle handling of the radiation source and the transport cable in the presence of obstacles in the transport cable, and particularly in the event of operator's errors, the irradiation apparatus can include an impact sensor for monitoring the shearing force exerted on the transport cable (claim 9) a detection of obstacles in the transport channel is already known per se from EP-A1-0 278 829. Of course, this impact sensor can also be used advantageously, independently of the other features of the aforementioned irradiation apparatus.

While the impact sensor can include any means for monitoring shearing force exerted on a cable, it is nevertheless advantageous for the impact sensor to include a region of the transport cable that is guided along a curve, as well as means for detecting a dislocation of the transport cable toward the outside of the curve (claim 8). Within the scope of this disclosure, the outside of the curve is understood to be the side of the cable facing radially outwardly from the curve.

Any sensors, for example optical or electrical sensors, for detecting a dislocation can serve as means for detecting the dislocation of a cable. The use of a mechanical switching contact and/or a proximity switch is especially advantageous, however.

If the radiation source or the transport cable impacts an obstacle as the radiation source advances, the transport cable in the region of the curve is dislocated toward the outside of the curve. The natural elasticity of the transport cable can suffice to prevent a dislocation of the transport cable toward the outside of the curve during normal operation, so the means for detecting a dislocation are not dislocated during normal operation. It can be advantageous, however, for the impact sensor to include elastic means that counteract a dislocation of the transport cable toward the outside of the curve. The shearing force to be exerted on the transport cable can be set by the selection of the spring constant. Examples of such elastic means include elastic-bending tubes that guide the transport cable. These tubes can also be rigid, but movable with respect to the rest of the transport cable, and can be connected to a retaining spring, for example a tension spring disposed on the inside of the curve. Of course, in a similar manner, a tensile-force sensor can be provided that monitors a dislocation of the transport cable toward the inside of the curve, for example. In such a case, elastic means can advantageously be provided that counteract the dislocation of the transport cable toward the inside of the curve.

In the use of a sensor that supplies an analog output signal for deflecting the curved transport cable, it is possible to use a servo amplifier to drive an electromagnet as a restoring force such that the deflection can be kept as small as desired. In this case, the servo amplifier supplies the signal necessary for monitoring the shearing force.

Of course, the transport-cable impact monitoring of the invention that has an impact sensor can also advantageously be used in irradiation apparatuses other than those described in claims 1, 3 and/or 4. A sensor having an analog output signal further permits a dynamic speed regulation:

The shortest possible extension time (<5 s) is necessary for minimizing the stress due to radiation. As the extension time increases, however, the frictional forces between the transport cable and the guide hose also increase, especially when the guide path has small radii of curvature.

The nominal value of the extension speed of the transport cable can be regulated with the analog sensor signal, corresponding to the frictional force, such that the shearing force exerted on the cable does not exceed a (cable-dependent), specific maximum value. Thus, an overstressing of the transport cable and the guide hose is prevented at the highest-possible extension speed. The advancing movement is only interrupted if the maximum permissible shearing force is exceeded at the minimum permissible extension speed. This dynamic speed regulation can also advantageously be used in irradiation apparatuses other than those described in claims 1, 3 and/or 4.

To prevent erroneous switches of the radiation sources, the transport container can include means, particularly electronic means, for identifying its associated radiation source (claim 9). Of course, these identification means can also be used advantageously, independently of the other features of the irradiation apparatus. In particular, these identification means can include an electronic memory, preferably a serial EEPROM (claim 10). Notably, it is possible to connect the rest of the irradiation apparatus with these identification means, particularly automatically, so the present radiation source can be identified by the irradiation apparatus, namely by its electronics. The identification means can also contain other data relating to the radiation source, such as initial activity and starting date, or the like. The identification means can also contain data relating to the transport container or the transport module. These data can be, for example, the length or strength of the transport cable. The identification means can likewise include data relating to the storage drum or the transport-cable drive, such as its radius or the number of path-indicator pulses per mm of extension path. In this way, high positioning precision is possible, despite low-cost production of the drive mechanics, which usually includes certain manufacturing tolerances, because the mechanical data can be compensated or settled by data contained by the identification means.

The shield can include assemblies comprising tungsten for meeting even higher shield requirements and increasing export opportunities, because this material possesses no characteristic radiation.

The aforementioned components are claimed and described in the exemplary embodiments, and are to be used in accordance with the invention, are not subjected to any exceptional conditions with regard to their size, shape, material selection and technical conception, so the selection criteria known in the respective field of use can be used without limitations.

Figure 2:
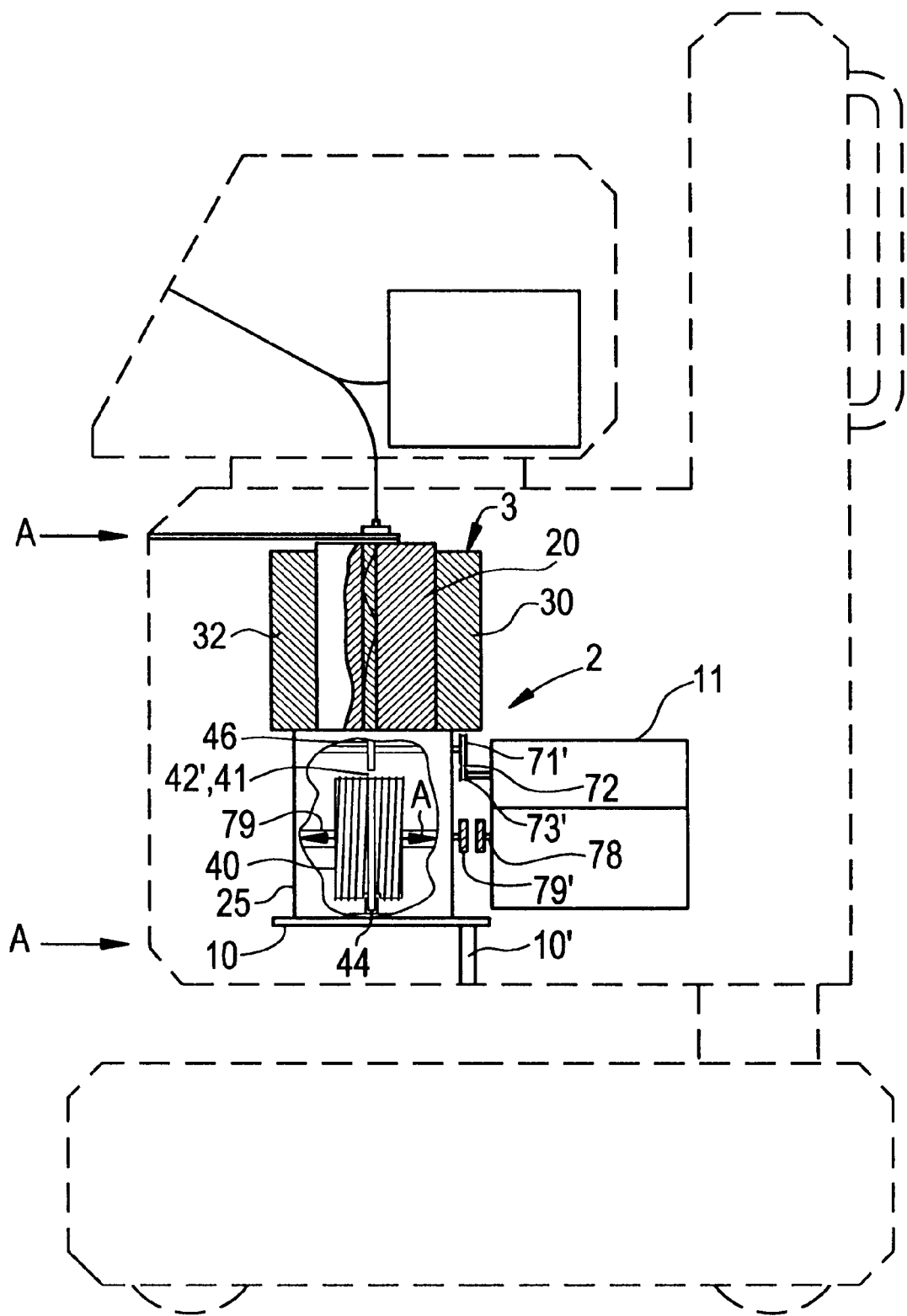
Figure 15A:
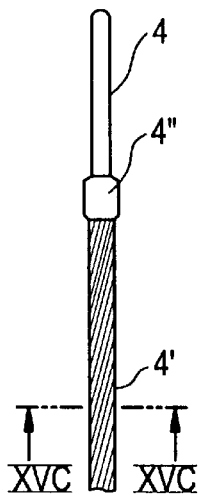
Figure 3:
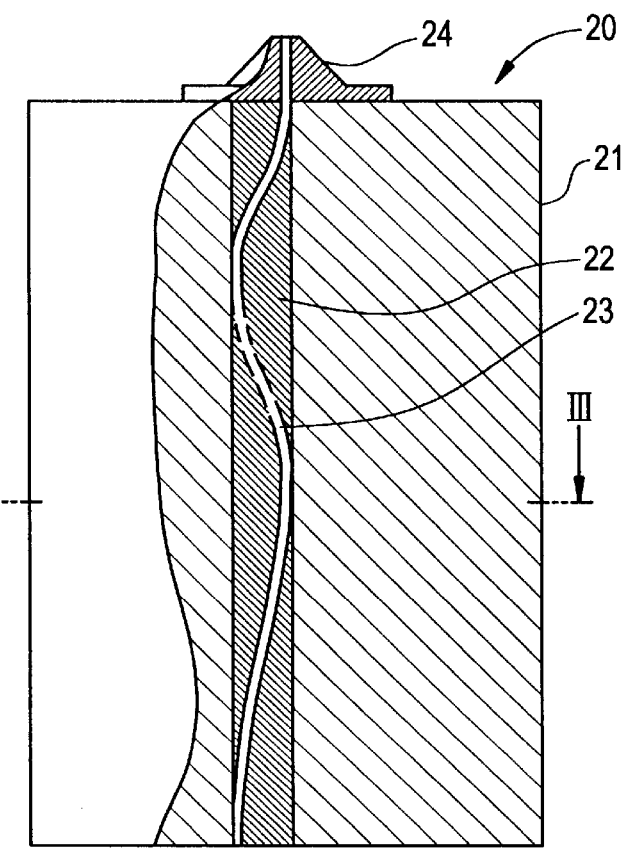
Figure 15B:
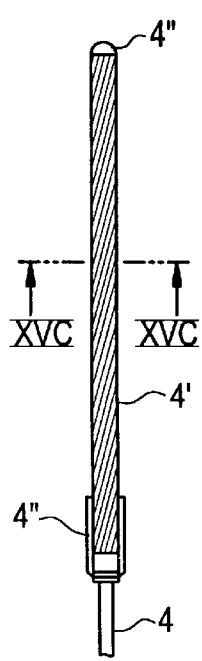
Figure 15C:
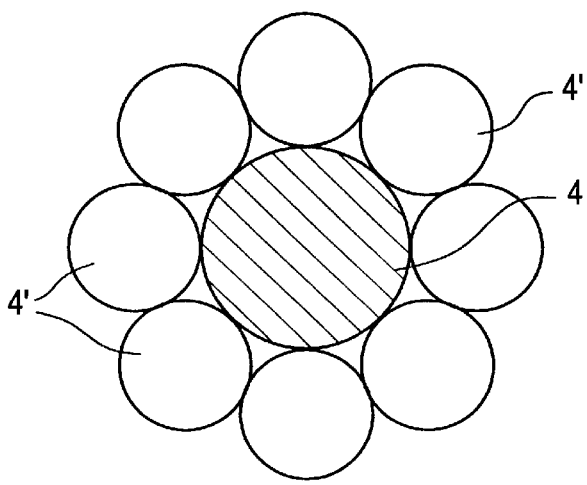
Figure 4:
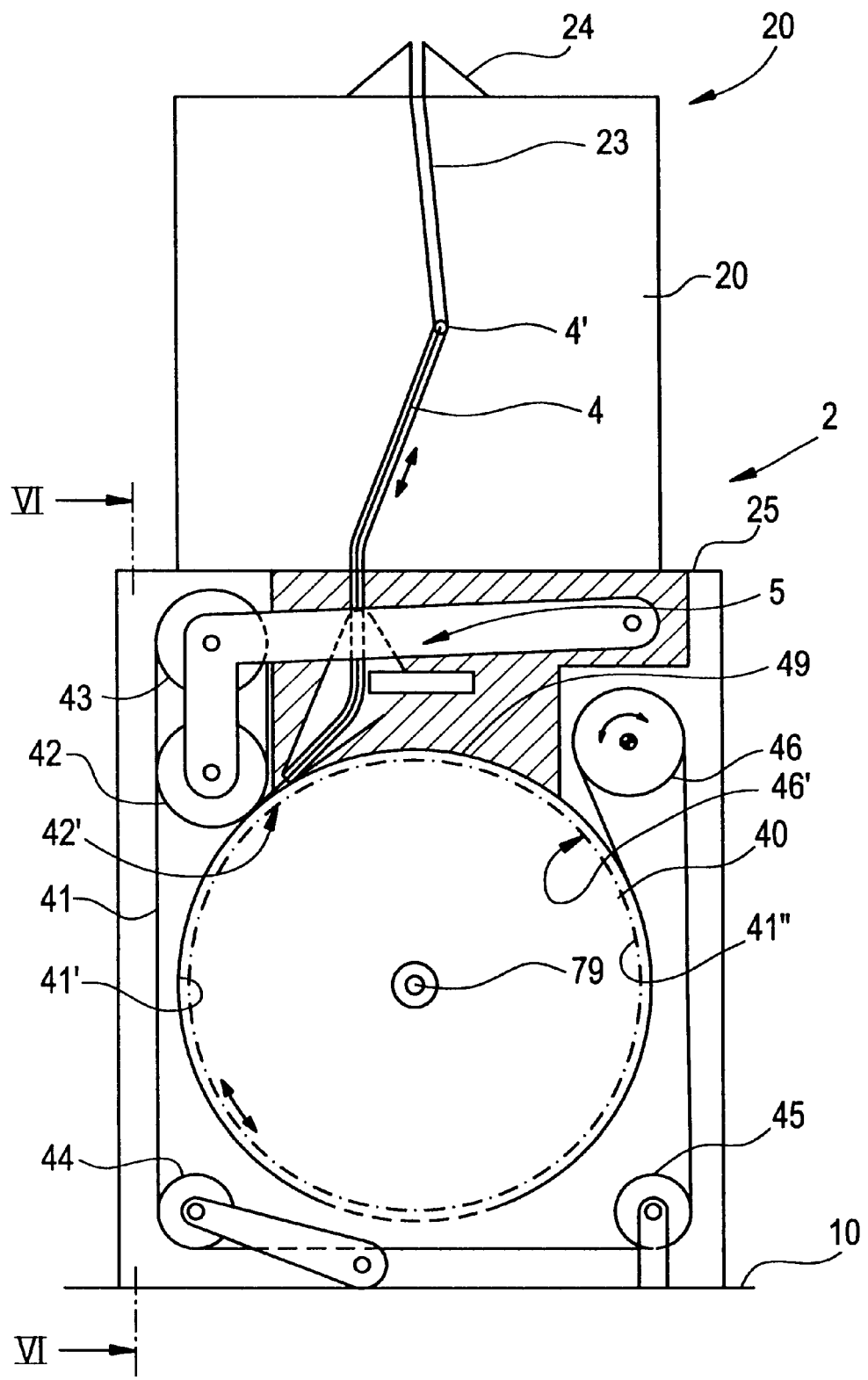
Figure 5:
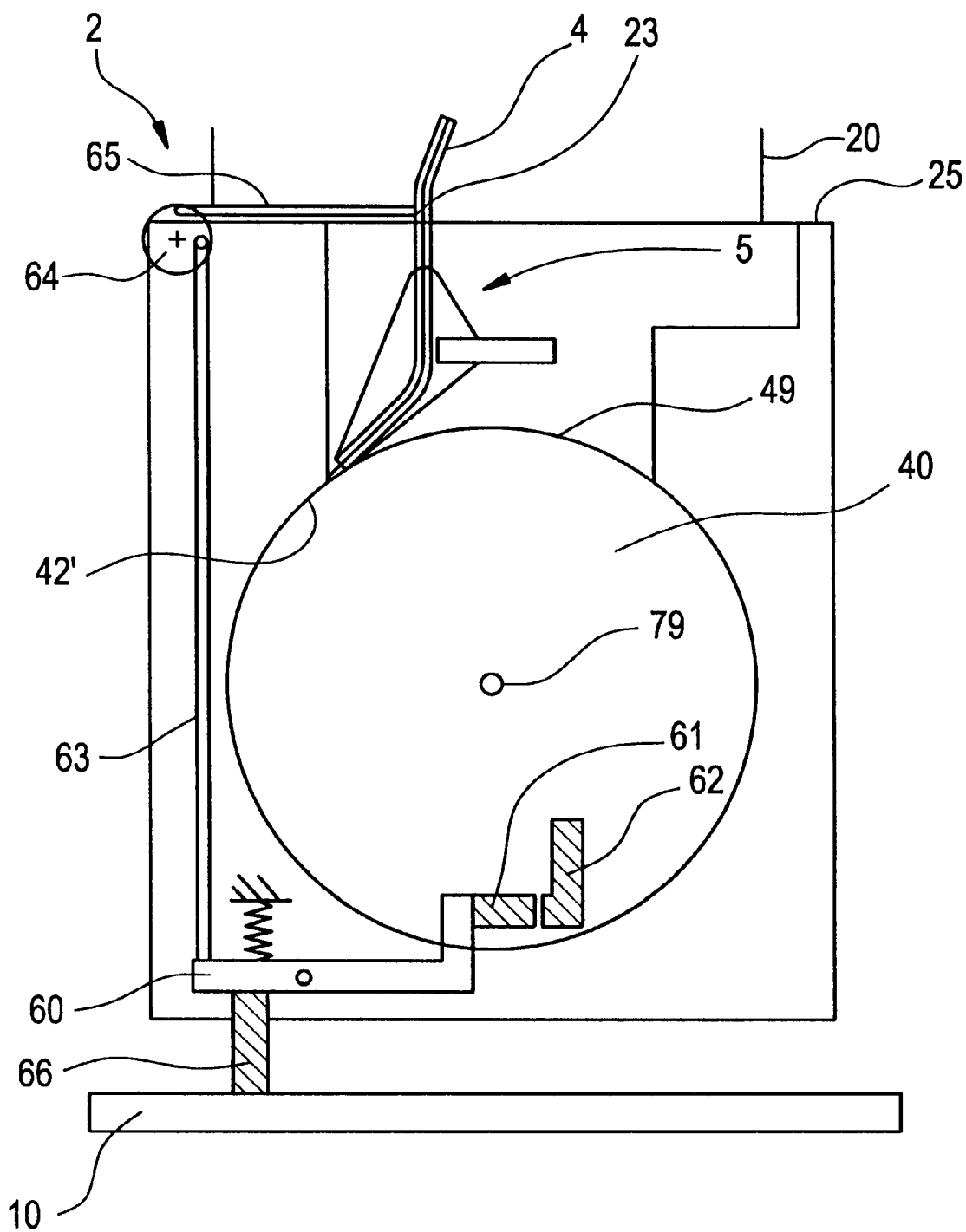
Figure 6:
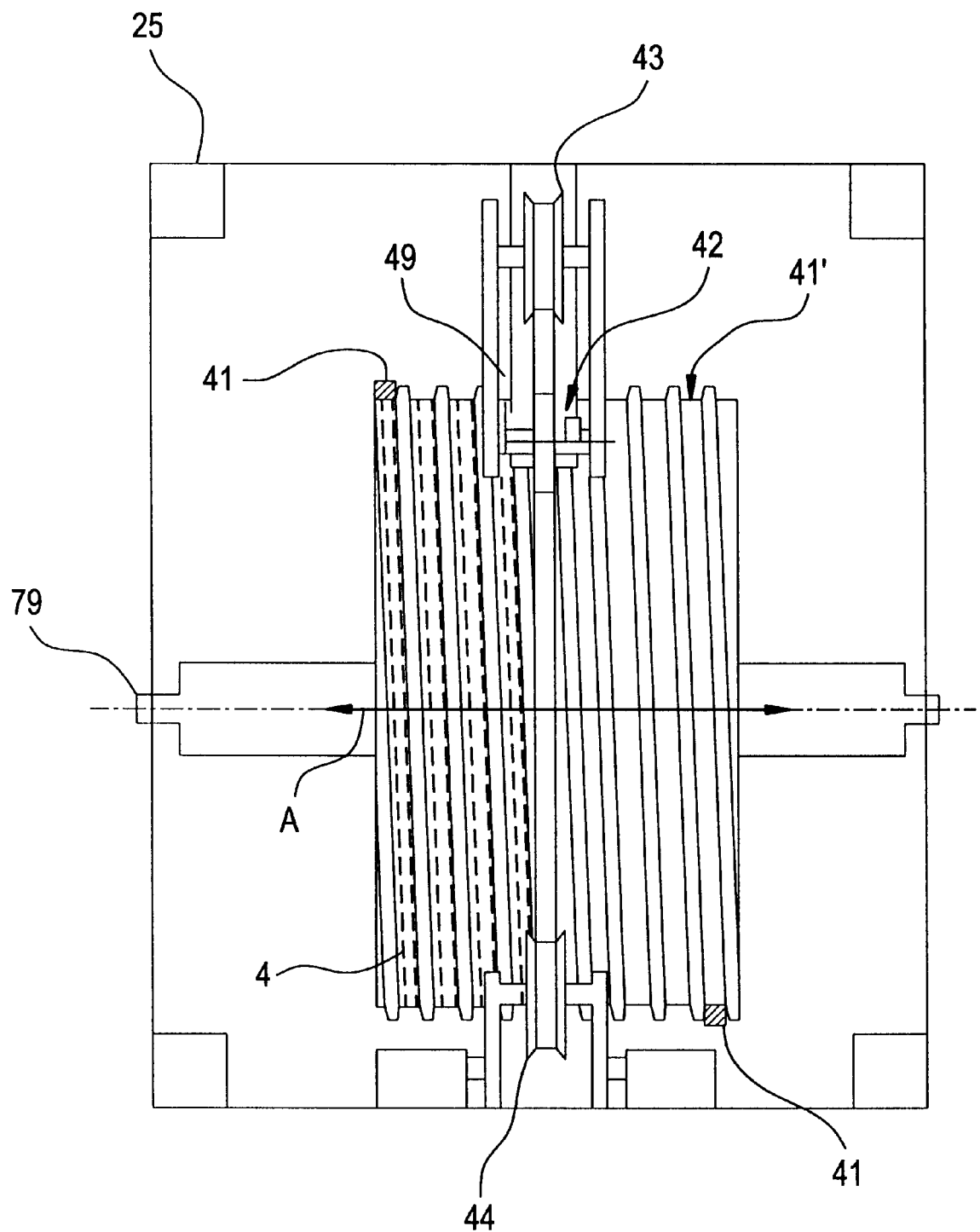
Figure 7:
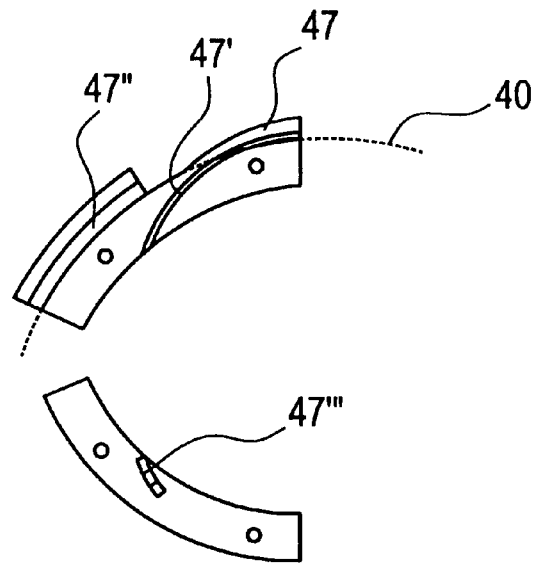
Figure 8:
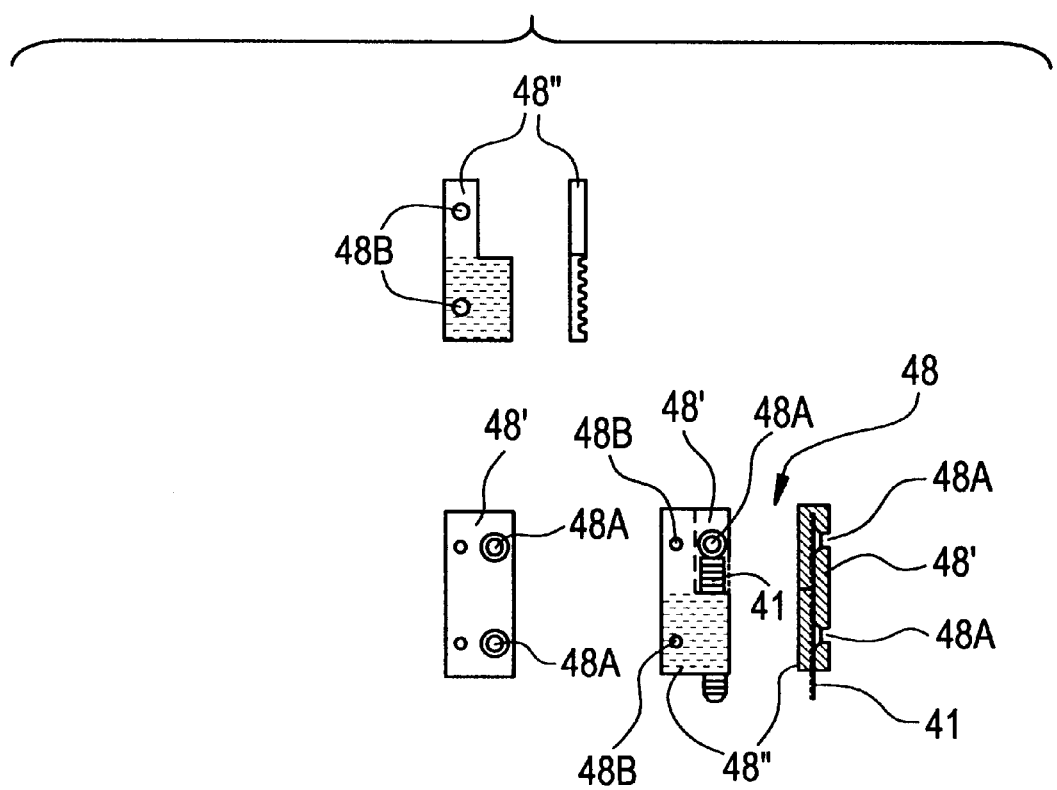
Figure 11:
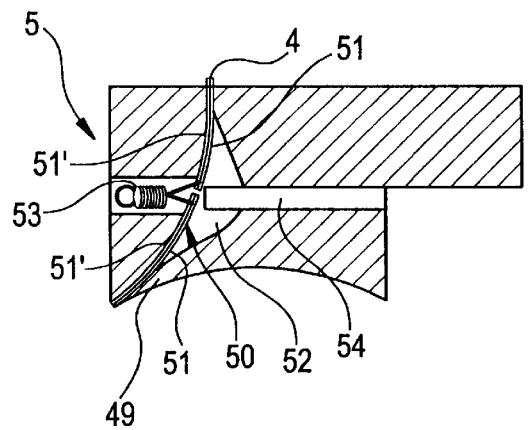
Figure 12:
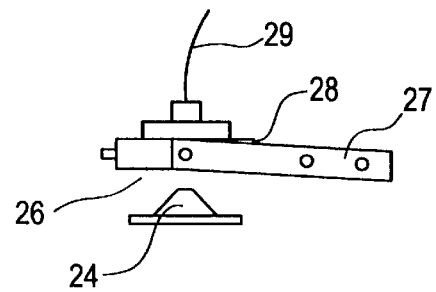
Figure 13:
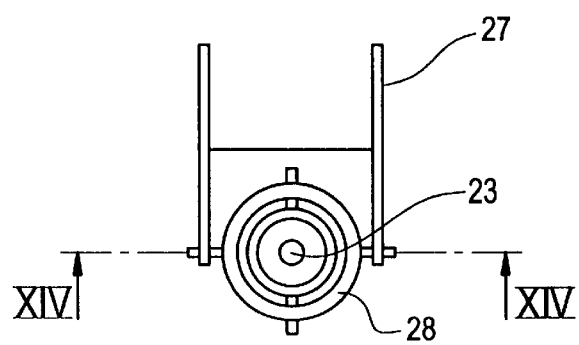
Figure 14:
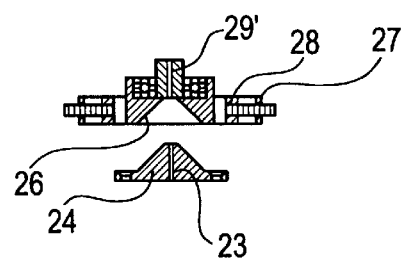
Figure 16:
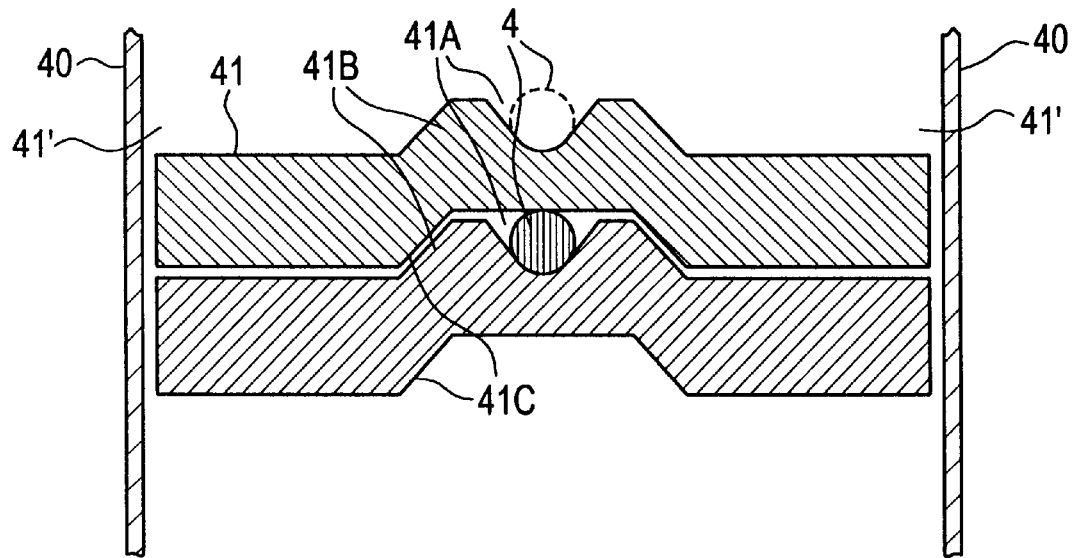
Figure 17:
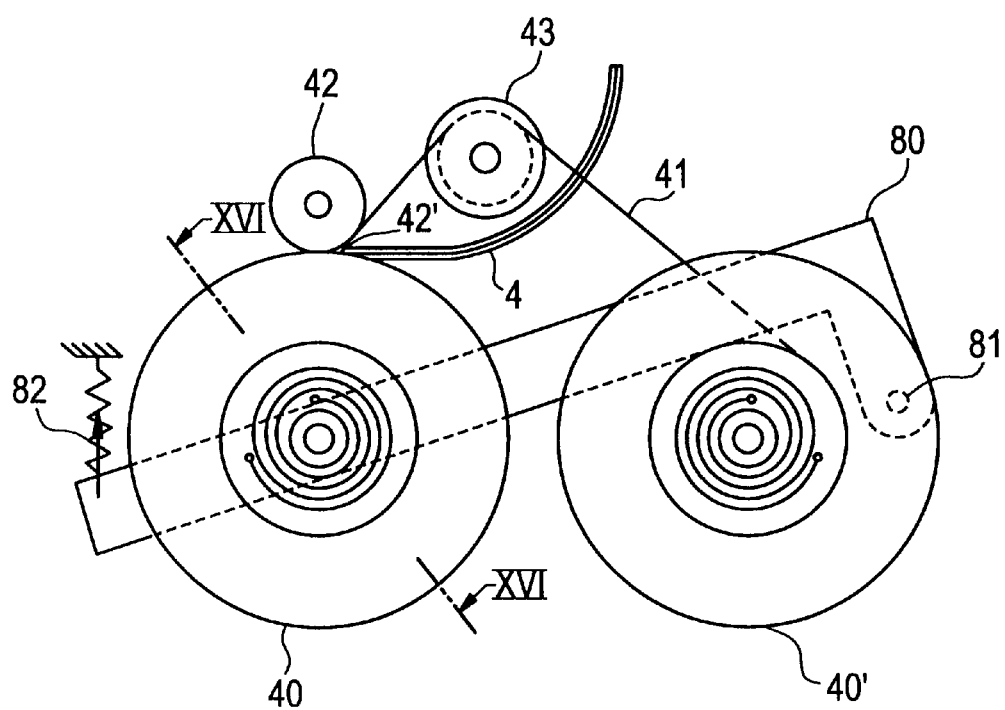
Figure 19:
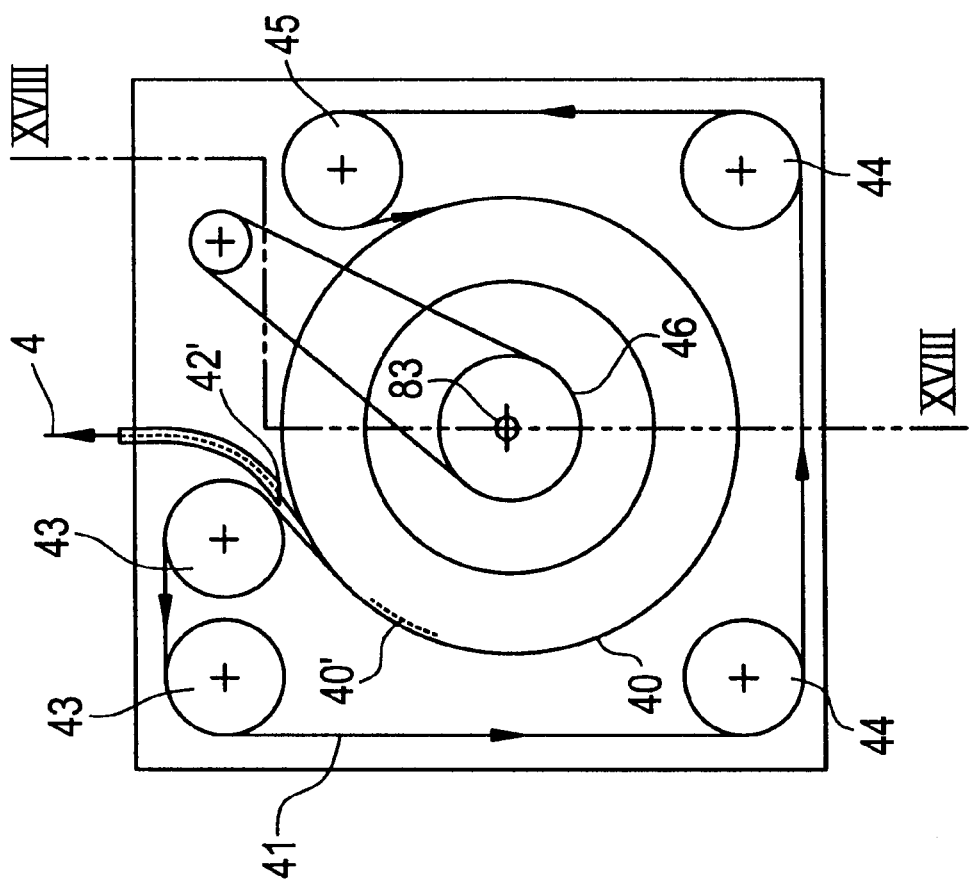
Figure 18:
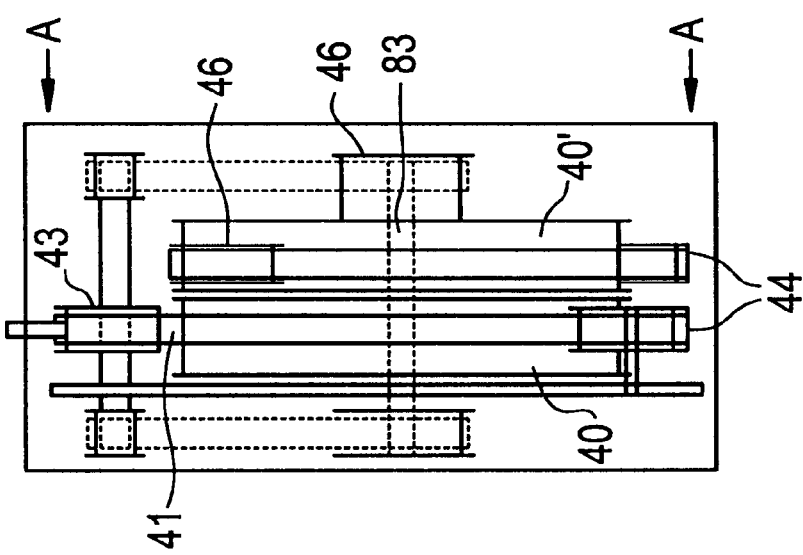

Further details, features and advantages of the subject of the invention ensue from the following description of the attached drawings, in which a preferred embodiment of an irradiation apparatus of the invention is shown by way of example. Shown are in:

FIG. 1 schematically, a plan view of an irradiation apparatus of the invention;

FIG. 2 the same irradiation apparatus in a side view, partially cut away and partially in vertical section;

FIG. 3 the transport container according to FIG. 2 in an enlarged side view, partially cut away;

FIG. 4 a front view of the transport module of FIGS. 1 through 3 (schematically and partially in vertical section)—view A—A according to FIGS. 1 and 2;

FIG. 5 schematically, the transport module of FIGS. 1 and 4 with locking means;

FIG. 6 the storage drum of the transport module of FIGS. 1 through 5, in section along the line VI—VI in FIG. 4;

FIG. 7 the securing of the transport cable and the pressing band to the storage drum;

FIG. 8 a clamping device for the pressing band;

FIG. 9 schematically, the transport-cable drive means of the irradiation apparatus of FIG. 1;

FIG. 10 the drive connection between the pressing band, the drive and the motor of the irradiation apparatus of FIG. 9, in section along the line X—X in FIG. 9;

FIG. 11 an impact sensor according to the invention;

FIG. 12 a transport-channel connector between the irradiation apparatus and a transport container;

FIG. 13 a plan view of the transport-channel connector of FIG. 12;

FIG. 14 the transport-channel connector of FIGS. 12 and 13, in section along the line XIV—XIV in FIG. 13;

FIGS. 15A–C two embodiments of a transport cable with a radiation source, in a side view (FIGS. 15A and 15B) and in cross-section (FIG. 15C);

FIG. 16 an alternative specific embodiment of the transport-cable guidance (alternative to FIG. 6) in an enlarged, cut-out representation of the cable-receiving groove (section along the line XVI—XVI according to FIG. 17);

FIG. 17 a side view of the same specific embodiment of a storage drum;

FIG. 18 a storage drum of the same specific embodiment for the specific embodiment of FIG. 16 (partially in axial section along the line XVIII—XVIII according to FIG. 19);

FIG. 19 a side view of the same storage drum (view A according to FIG. 18); and

FIG. 20 a side view of a storage drum as an additional alternative to the specific embodiment of FIG. 16.

As shown in FIG. 1, the irradiation apparatus has a carrier plate 10, on which a transport module 2 that has a transport container 20 is disposed. Carrier plate 10 can pivot horizontally about a shaft 10' to facilitate the removal and insertion of transport module 2 (the outward-pivoted position is shown as a dashed line in FIG. 1). In the inward-pivoted state, the transport container is enveloped by an additional shield 3. Additional shield 3 has an additional-shield half 30, which is permanently connected to the irradiation apparatus, and an additional-shield half 32, which can swing out by means of a hinge 31. The two additional-shield halves 30 and 32 are embodied such that, when hinge 31 is in the open state, transport module 2 can pivot outward with carrier plate 10. However, the cuts of the two additional-shield halves 31 [sic] and 32 are configured such that the section planes do not intersect at least the storage position. of the radiation source, and possibly even transport container 20 (as shown in FIG. 1 and preferred in this regard). This prevents radiation from exiting along the section planes.

The irradiation apparatus further has a housing 11 for diverse drives, at least for a transport cable, and diverse control units.

Transport container 20 preferably includes an outside cylinder 21, which is bored through eccentrically and preferably comprises tungsten, and in which an inside cylinder 22 fits. A spiral-shaped cable channel is cut into the outside surface of inside cylinder 22. A transport and radiation-protection container of this type can also be used advantageously without the features of the dependent claims, and can be manufactured simply. This spiral-shaped cable channel 23 exits transport container 20 through a connecting cone 24 disposed on a surface of the cylinder formed by outside cylinder 21 and inside cylinder 22.

As FIG. 4 shows, transport module 2 has beneath its transport container 20 a drive housing 25, in which assemblies for driving a transport cable 4 are disposed. A radiation source 4' is disposed at one end of transport cable 4. FIG. 4 shows radiation source 4' in its non-operative position.

Disposed in drive housing 25 is a storage drum 40, onto and from which transport cable 4 can be wound and unwound. As explained below, transport cable 4 is pressed on storage drum 40 by a pressing band 41. A pressing roller 42, by way of which pressing band 41 is lifted from storage drum 40, is provided in the region of lifting point 42'. Pressing band 41 is guided back to storage drum 40 by means of deflection rollers 43, 44 and 45 and a drive roller 46. As is preferred, the side of pressing band 41 that rests against drive roller 46 is embodied as a toothed belt, which assures reliable driving of pressing band 41, and thus of storage drum 40 and transport cable 4.

Behind lifting point 42', prior to entrance into transport container 20, transport cable 4 has a curved region, which forms a further impact sensor 5 that is described below.

During normal operation, pressing band 41 is driven by means of drive roller 46, so that transport cable 4 is unwound from storage drum 40. In this way, radiation source 4' is moved out of its non-operative position, through the spiral-shaped cable channel 23 and connecting cone 24, and into a radiating position. Conversely, radiation source 4' can be moved back into its non-operative position by corresponding driving of drive roller 46.

For securing radiation source 4' in its transport position during transport of transport module 2, the source has a stop lever 60 (FIG. 5) and a stop 62 on drive housing 25, between which a pin 61 located on storage drum 40 can be stopped when radiation source 4' is in its transport position. Stop lever 60 is further connected to a stop rod 63, which, by means of a gear 64, can press a further stop rod 65 into spiral-shaped cable channel 23, thus stopping transport cable 4.

If transport module 2 is positioned on carrier plate 10, stop lever 60 can be pivoted by means of an unlocking pin 66. This pivoting stipulates that stop rod 65 releases transport cable 4 (FIG. 5). This pivoting of stop lever 60 also effects the release of storage drum 40 by pin 61 (this released state has not yet been attained in the representation of FIG. 5). If stop lever 60 has released pin 61, the storage drum can extend radiation source 4'. Storage drum 40 is displaced—as will be explained below in connection with FIG. 6—as it rotates, that is, during the movement of transport cable 4 parallel to the shaft 79 of the storage drum. Therefore, with respect to stop 62, pin 61 already has sufficient spacing to permit free rotation of storage drum 40 after one drum rotation.

The spiral-shaped arrangement of pressing band 41 in a spiral-shaped cable-receiving groove 41' of storage drum 40 is shown schematically in FIG. 6. This figure shows pressing band 41 in section at the end of cable-receiving groove 41'. While pressing band 41 is guided in cable-receiving groove 41' over practically the entire length of the groove, in FIG. 6, transport cable 4 is only wound in the left region onto storage drum 40 (shown in a dashed line). In the region of lifting point 42' of the transport channel, pressing band 41 is also lifted from storage drum 40 by means of pressing roller 42 and deflection rollers 43, 44 and 45 and drive roller 46. As shown particularly in FIG. 6, pressing band 41 extends essentially in a plane perpendicular to storage-drum shaft 79. A guide part 49, which slides into cable-receiving groove 41', 41' as a guide shoe and is fixed to the housing, forces rotating storage drum 40 to perform a relative movement with respect to lifting point 42', so that storage drum 40 slides along its shaft (shaft 79) in the illustrated, preferred exemplary embodiment.

Storage drum 40 is disposed to be displaced—namely, to slide—on storage-drum shaft 79, as indicated by the double-headed arrow A. In this way, lifting point 42' and the positions of pressing roller 42, deflection rollers 43, 44, 45 and drive roller 46 remain stationary, while, at 46', pressing band 41 returns into the pressing position in the part of cable-receiving groove 41'' adjacent to lifting point 42.

Mounted on the one side of storage drum 40 (shown as a dashed line in FIG. 7) is a holding element 47 that has a clamping channel 47' for transport cable 4 and a pressing-band holding element 47''. A transport-band clamp 47''' is also mounted on this side of the storage drum, the clamp fixing transport band 4 with respect to storage drum 40. Mounted to the other side of storage drum 40 is a tensing device 48 for pressing band 41, which device includes a base plate 48' secured to storage drum 40 by means of screws 48A and onto which a clamping plate 48'' having recesses that correspond to the toothing of the pressing band is fastened by means of screws 48B, so that the toothing of pressing band 41 engages the recesses and, in this way, the band is fixed in its position.

As FIG. 9 shows, in a normal case, drive roller 46 and thus transport cable 4 are driven by way of a drive shaft 71 that is connected, fixed against relative rotation, to the roller, and a drive disk 71' that is connected to the drive shaft. Drive disk 71' has a toothing, which is engaged by a toothed belt 72. During operation, toothed belt 72 runs over a drive disk 73' mounted on a motor 73. Motor 73 can move between an ON position and an OFF position by way of a tension spring 73''' and a pressure magnet 73''' such that, in the currentless state of pressure magnet 73''', drive disk 73' does not engage toothed belt 72, whereas pressure magnet 73''' brings drive disk 73' into engagement with toothed belt 72 during a current flux (FIG. 10). In an emergency, particularly in a power failure, drive shaft 71 is separated from motor 73 by this measure, and can be moved freely, for example to rewind transport cable 4 on storage drum 40. Even in the OFF position, removal of transport module 2 is very simple, because the module need not be separated from the transport-cable drive in a special step.

To permit transport cable 4 and thus radiation source 4' to be brought into, for example, the transport or non-operative position in an emergency, the irradiation apparatus has an emergency drive. The emergency drive includes a coupling disk 79', which is connected to the storage-drum shaft 79 embodied as a torque shaft. A second coupling disk 78' is connected to a shaft 78, with shaft 78 being pressed with coupling disk 78' against the first coupling disk 79' by means of a compression spring 77. In contrast, coupling disks 78' and 79' are separated by means of a pull-type electromagnet 76, so that when current flows through pull-type electromagnet 76, the emergency drive is separated from the storage-drum shaft. Pull-type electromagnet 76 can release shaft 78 and thus couple in the emergency drive, particularly in the case of a power failure, but also, for example, through manual operation. For moving the transport cable, the emergency drive has a crank handle 74 and an emergency motor 75, which are connected to shaft 78 by way of toothed wheels 78".

Of course, the individual features of the aforementioned transport-cable drive can be used advantageously, independently of the other features of the irradiation apparatus.

Impact sensor 5 includes a curved region 50 of transport cable 4, which is guided in this curved region 50 in two elbows 51, which preferably have a bending radius of 4 cm and are spaced slightly from one another. Elbows 51 rest against stops 51' on the inside of the curve, but can be dislocated into a hollow space 52 provided on the outside of the curve. A tension spring 53 holds elbows 51 in their position with respect to stops 51'. If transport cable 4 impacts an object as it advances, it has the tendency to be dislocated into hollow space 52, that is, toward the outside of the curve. If the force exerted on elbows 51 by this movement exceeds the tensile force of tension spring 53, transport cable 4 and elbows 51 are dislocated into hollow space 52. This dislocation is detected by a switch 54. Switch 54 transmits a signal to the electronics of the irradiation apparatus, which prevents further pushing of transport cable 4 through storage drum 40.

Transport container 20 has connecting cone 24, through which spiral-shaped cable channel 23 exits, for ensuring a connection between spiral-shaped cable channel 23 of the transport container and a connecting hose 29 that functions reliably and can be produced and released quickly. Moreover, the irradiation apparatus has a connecting cone 26, which can be placed onto connecting cone 24 (FIGS. 12 through 14). To increase the operator's comfort and the operating reliability, connecting cone 26 is connected to the rest of the irradiation apparatus by means of a movable arm 27. To ensure precise placement of connecting cone 26 on connecting cone 24, connecting cone 26 is connected to arm 27 by way of a cardan joint 28.

In the center, connecting cone 26 has a cable channel 29', which transitions into a connecting hose 29. Cable channel 29' is disposed in a connecting piece 26' that is connected to the rest of connecting cone 26 by way of a ball bearing 26" for ensuring that connecting hose 29 can rotate with respect to connecting cone 26. The forces acting on connecting hose 29 and the connection between connecting cone 26 and connecting cone 24 can be reduced with this measure.

Of course, with this type of connection of a transport container 20 with a connecting hose 29, a reliably functioning, easy-to-operate connection of a transport container 20 with a connecting hose 29 can also be effected independently of the other features of the irradiation apparatus.

Extremely thin transport cables and short-range radiation sources in fiber form, particularly beta radiators, as are basically known from EP-A1-0 633 041, can be used with the storage drum according to the invention having a spiral-shaped pressing band. FIG. 15A shows the tip of a transport cable 4 of this type, which can also be curved in a J-shape, for example, for guiding a catheter around narrow curves. A glued, pressed or welded point 4" produces the connection between the fiber-type radiation sources 4' and drive cable 4. FIG. 15B shows a corresponding radiation source without a guide tip, and FIG. 15C shows a cross-section.

In the specific embodiments of FIGS. 16 through 20, the spiral-type winding of transport cable 4 and pressing band 41 respectively covering only one winding of the transport cable is effected in a radial direction with respect to storage drum 40, so that transport cable 4 is guided narrowly between the part of an uninterrupted pressing band that covers and presses the cable radially from the outside and the radial outside of the winding of pressing band 41 that is respectively closest to the shaft. For this purpose, the two radially outside surfaces of pressing band 41 possess the complementary surface configuration that can be seen in FIG. 16, namely the preferred groove/spring arrangement of FIG. 16 that has a transport-cable guide groove 41A on the side of the "spring" 41B.

This transport-cable and pressing-band guidance can be effected in various forms. For example, the part of the pressing band that does not yet cover or no longer covers the transport cable can be wound onto or unwound from a storage drum 40'. These specific embodiments are illustrated in FIGS. 17 through 20.

To take into consideration the different radii, such as inevitably occur at the exit point 42' of the transport cable from storage drum 40 because of the "radial" unwinding process, in the specific embodiment of FIG. 17, it is provided that the two storage drums 40 and 40' are rotatably seated on a common rocker 80, on shafts that are spaced from one another. Exit point 42' remains fixed to the apparatus while storage drums 40 and 40' are guided behind, about the rotation point 81 of rocker 80 under the pulling force of a spring 82, corresponding to the increase or decrease in the radius of transport cable 4 and pressing band 41.

The pressing band must guide the transport cable reliably under all operating conditions. Therefore, the pressing band should be subjected to a certain tensile stress. This tensile stress can be exerted, for example, by flat coil springs located in storage spools 40 and 40', which springs counteract one another; the spring force of the restoring coil should always be greater than the force of the advancing coil (FIG. 17).

Another option is to generate the tensile stress through pre-stressed rollers that act on the pressing band (FIGS. 18 and 19). This is only possible, however, if the two spools 40 and 40' are mechanically coupled to one another. For this purpose, spools 40 and 40' are rotatably secured on a common drive shaft 23 [sic] in the specific embodiment of FIGS. 18 and 19. It is therefore necessary to dispose deflection rollers 43, 44 and 45 of pressing band 41 such that the pressing band can be guided back and forth between the storage drums 40 and 40' disposed with axial spacing—such as in a gear shift of a bicycle, but with only driving wheels and no driven wheels.

Because of the changeable winding diameter on storage drums 40 and 40', the relative speed of storage drums 40 and 40' must change during winding and unwinding of the pressing band if the guidance path of pressing band 41 between the two storage drums is to be kept constant. A relative speed corresponding to the winding diameter can be attained with a gear having two spiral-shaped toothed wheels Z3 and Z4 according to FIG. 20. When pressing band 41 is wound, for example, in ten layers from storage drum 40 onto storage drum 40', the total rotation path of storage drum 40 can be transformed into a single revolution of the two spiral-shaped toothed wheels Z3 and Z4 through a gear reduction of 10:1 by means of toothed wheels Z1:Z2 or Z6:Z5. The variable transmission ratio of these two toothed wheels is selected such that the unwinding and winding speed of the two storage drums 40 and 40' is not a function of the winding diameter.

LIST OF REFERENCE NUMERALS

| 10 | carrier plate | 41A | transport-cable guide groove |
|---|---|---|---|
| 10' | shaft | | |
| 11 | drive housing | 41' | cable-receiving groove |
| 2 | transport module | 41" | cable-receiving groove |
| 20 | transport container | 41B | spring |
| 21 | outside cylinder | 41C | groove |
| 22 | inside cylinder | 42 | pressing roller |
| 23 | spiral-shaped cable channel | 42' | exit point |
| 24 | connecting cone | 43 | deflection roller |
| 25 | drive housing | 44 | deflection roller |
| 26 | connecting cone | 45 | deflection roller |
| 27 | arm | 46 | drive roller |
| 28 | cardan joint | 47 | holding element |
| 29 | connecting hose | 47' | clamping channel |
| 29' | cable channel of connecting cone | 47" | pressing-band holding element |
| 3 | additional shield | | |
| 30 | additional-shield half, stationary | 48 | tensing device |
| | | 48' | base plate |
| 31 | hinge | 48" | clamping plate |
| 32 | additional-shield half, hinged | 48A | screws |
| 4 | transport cable | 48B | screws |
| 4' | radiation source | 49 | guide part |
| 4" | glued, pressed or welded point | 5 | impact sensor |
| 40 | storage drum | 50 | curved region |
| 40' | storage drum | 51 | elbows |
| 41 | pressing band | 51' | stop |
| 62 | stop | 52 | hollow space |
| 63 | stop rod | 53 | tension spring |
| 64 | gear | 54 | switch |
| 65 | stop rod | 60 | stop lever |
| 66 | unlocking pin | 61 | pin |
| 71 | drive shaft | | |
| 71' | drive disk | | |
| 72 | toothed belt | | |
| 73 | motor | | |
| 73' | drive disk | | |
| 73" | tension spring | | |
| 73''' | pressure magnet | | |
| 74 | crank handle | | |
| 75 | emergency motor | | |
| 76 | pull-type electromagnet | | |
| 77 | compression spring | | |
| 78 | shaft | | |
| 78' | coupling disk | | |
| 78" | toothed wheel | | |
| 79 | storage-drum shaft | | |
| 79' | coupling disk | | |
| 80 | rocker | | |
| 81 | rotation point | | |
| 82 | spring | | |
| 83 | drive shaft | | |

Having thus described the invention, it is claimed:

1. An irradiation apparatus having at least one exchangeable radiation source that can be moved between at least one non-operative position, which is located inside of a shield in the irradiation apparatus, and at least one radiating position, which is located outside of the shield, by means of a transport cable, the apparatus further having a radiation-source transport container for long-distance transport of exchangeable radiation sources completely separate from the irradiation apparatus, the improvement comprising the radiation-source transport container being a component of the irradiation apparatus that is detachably integrated, and an interface means that allows the radiation-source transport container to be integrated, being provided on the container, and on the other part of the irradiation apparatus, so the radiation-source transport container serves as a shield or a part of the shield of the irradiation apparatus in which the non-operative position is located, wherein the irradiation apparatus has a shield that surrounds at least parts of the transport container and that the transmitted radiation of the irradiation apparatus meets the specifications for radiation-source storage containers when the radiation source is in its non-operative position.

2. The irradiation apparatus as defined in claim 1, wherein, said transport cable storage element includes a storage drum, onto or from which the transport cable can be wound and unwound, respectively.

3. The irradiation apparatus as defined in claim 1, wherein the radiation-source transport container or the transport module includes path indicators means for determining the position of the radiation source.

4. The irradiation apparatus as defined in claim 1, wherein the radiation-source transport container (20) includes a tungsten shield that is bored through eccentrically.

5. The irradiation apparatus as defined in claim 1, including means for automatically locking the radiation source or the transport cable in a transport position during transport of the radiation-source transport container.

6. The irradiation apparatus as defined in claim 1, including a dynamic speed regulation of the transport cable in cooperation with a sensor that detects traveling resistance.

7. A method of intra-arterial irradiation for preventing a post-angioplasty or other potential restenosis, comprising the use of an irradiation apparatus as defined in claim 1.

8. The irradiation apparatus as defined in claim 1, wherein the radiation-source transport container or a transport module includes, as a component of the irradiation apparatus, electronic means for identifying the radiation source and for identifying characterizing variables of the storage drum.

9. The irradiation apparatus as defined in claim 8, wherein the identification means includes an electronic memory.

10. The irradiation apparatus as defined in claim 1, wherein the radiation-source transport container comprises an outside cylinder, an inside cylinder that fits inside a bore in the outside cylinder, said bore being disposed asymmetrically, and a spiral-shaped cable channel cut into the contact surface between the inside cylinder and the bore in the outside cylinder, as a radially outer groove in the outside surface of the inside cylinder.

11. The irradiation apparatus as defined in claim 1, wherein the transport cable is wound onto or unwound from a storage drum having a cable-receiving groove that is at least partially covered by a pressing band, wherein the width of the pressing band corresponds to the width of the cable-receiving groove, that the pressing band is wound, in spiral fashion in the cable-receiving groove, around the storage drum in the axial or radial direction with respect to the storage drum, and essentially covers the cable-receiving groove without interruption, and that a device for lifting, deflecting and repositioning, the pressing band for freeing an exit point for the transport cable to the storage drum can travel along the drum and relative to it.

12. The irradiation apparatus as defined in claim 1, wherein the irradiation apparatus further includes an impact sensor for monitoring the shearing force exerted on the transport cable.

13. An irradiation apparatus having at least one exchangeable radiation source that can be moved between at least one non-operative position, which is located inside of a shield in the irradiation apparatus, and at least one radiating position, which is located outside of the shield, by means of a transport cable, the apparatus further having a radiation-source transport container for long-distance transport of exchangeable radiation sources completely separate from the irradiation apparatus, the improvement comprising the radiation-source transport container being a component of the irradiation apparatus that is detachably integrated, and an interface means that allows the radiation-source transport container to be integrated, being provided on the container, and on the other part of the irradiation apparatus, so the radiation-source transport container serves as a shield or a part of the shield of the irradiation apparatus in which the non-operative position is located, wherein the radiation-source transport container or a transport module includes, as a component of the irradiation apparatus, electronic means for identifying the radiation source and for identifying characterizing variables of the storage drum.

14. The irradiation apparatus as defined in claim 13, wherein the identification means includes an electronic memory.

15. The irradiation apparatus as defined in claim 14, wherein the electronic memory is a serial EEPROM.

16. The irradiation apparatus as defined in claim 13, wherein the transport cable is wound onto or unwound from a storage drum having a cable-receiving groove that is at least partially covered by a pressing band, wherein the width of the pressing band corresponds to the width of the cable-receiving groove, that the pressing band is wound, in spiral fashion in the cable-receiving groove, around the storage drum in the axial or radial direction with respect to the storage drum, and essentially covers the cable-receiving groove without interruption, and that a device for lifting, deflecting and repositioning, the pressing band for freeing an exit point for the transport cable to the storage drum can travel along the drum and relative to it.

17. The irradiation apparatus as defined in claim 13, wherein the radiation-source transport container or the transport module includes path indicators means for determining the position of the radiation source.

18. The irradiation apparatus as defined in claim 13, wherein the irradiation apparatus further includes an impact sensor for monitoring the shearing force exerted on the transport cable.

19. An irradiation apparatus having at least one exchangeable radiation source that can be moved between at least one non-operative position, which is located inside of a shield in the irradiation apparatus, and at least one radiating position, which is located outside of the shield, by means of a transport cable, the apparatus further having a radiation-source transport container for long-distance transport of exchangeable radiation sources completely separate from the irradiation apparatus, the improvement comprising the radiation-source transport container being a component of the irradiation apparatus that is detachably integrated, and an interface means that allows the radiation-source transport container to be integrated, being provided on the container, and on the other part of the irradiation apparatus, so the radiation-source transport container serves as a shield or a part of the shield of the irradiation apparatus in which the non-operative position is located, wherein the radiation-source transport container comprises an outside cylinder, an inside cylinder that fits inside a bore in the outside cylinder, said bore being disposed asymmetrically, and a spiral-shaped cable channel cut into the contact surface between the inside cylinder and the bore in the outside cylinder, as a radially outer groove in the outside surface of the inside cylinder.

20. The irradiation apparatus as defined in claim 19, wherein the radiation-source transport container including a tungsten shield that is bored through eccentrically.

21. The irradiation apparatus as defined in claim 18, including a dynamic speed regulation of the transport cable in cooperation with a sensor that detects traveling resistance.

22. The irradiation apparatus as defined in claim 19, including means for automatically locking the radiation source or the transport cable in a transport position during transport of the radiation-source transport container.

23. An irradiation apparatus having at least one exchangeable radiation source that can be moved between at least one non-operative position, which is located inside of a shield in the irradiation apparatus, and at least one radiating position which is located outside of the shield, by means of a transport cable, the apparatus further having a radiation-source transport container for long-distance transport of exchangeable radiation sources completely separate from the irradiation apparatus, the improvement comprising the radiation-source transport container being a component of the irradiation apparatus that is detachably integrated, and an interface means that allows the radiation-source transport container to be integrated, being provided on the container, and on the other part of the irradiation apparatus, so the radiation-source transport container serves as a shield or a part of the shield of the irradiation apparatus in which the non-operative position is located, wherein the transport cable is wound onto or unwound from a storage drum having a cable-receiving groove that is at least partially covered by a pressing band, wherein the width of the pressing band corresponds to the width of the cable-receiving groove, that the pressing band is wound, in spiral fashion in the cable-receiving groove, around the storage drum in the axial or radial direction with respect to the storage drum, and essentially covers the cable-receiving groove without interruption, and that a device for lifting, deflecting and repositioning, the pressing band for freeing an exit point for the transport cable to the storage drum can travel along the drum and relative to it.

24. The irradiation apparatus as defined in claim 23, wherein a guide part is provided in the region of a transport-cable exit point and extends into the cable-receiving groove, and at least guides the transport cable into or out of the cable-receiving groove.

25. The irradiation apparatus as defined in claim 23, including a dynamic speed regulation of the transport cable in cooperation with a sensor that detects traveling resistance.

26. The irradiation apparatus as defined in claim 23, including means for automatically locking the radiation source or the transport cable in a transport position during transport of the radiation-source transport container.

27. The irradiation apparatus as defined in claim 23, wherein the radiation-source transport container including a tungsten shield that is bored through eccentrically.

28. An irradiation apparatus having at least one exchangeable radiation source that can be moved between at least one non-operative position, which is located inside of a shield in the irradiation apparatus, and at least one radiating position, which is located outside of the shield, by means of a transport cable, the apparatus further having a radiation-source transport container for long-distance transport of exchangeable radiation sources completely separate from the irradiation apparatus, the improvement comprising the radiation-source transport container being a component of the irradiation apparatus that is detachably integrated, and an interface means that allows the radiation-source transport container to be integrated, being provided on the container, and on the other part of the irradiation apparatus, so the radiation-source transport container serves as a shield or a part of the shield of the irradiation apparatus in which the non-operative position is located, said irradiation apparatus including an impact sensor for monitoring the shearing force exerted on the transport cable.

29. The irradiation apparatus as defined in claim 28, wherein the impact sensor includes a region of the transport cable that is guided along a curve, and means for detecting a dislocation of the transport cable toward the outside of the curve.

30. The irradiation apparatus as defined in claim 28, including a region of the transport cable that is at least curved has two free ends at an interruption point.

31. The irradiation apparatus as defined in claim 30, including at least one restoring spring that acts on at least one of the free ends for establishing a deflection force.

32. The irradiation apparatus as defined in claim 28, wherein the radiation-source transport container or the transport module includes path indicators means for determining the position of the radiation source.

33. The irradiation apparatus as defined in claim 28, wherein the radiation-source transport container includes a tungsten shield that is bored through eccentrically.

34. The irradiation apparatus as defined in claim 28, including a dynamic speed regulation of the transport cable in cooperation with a sensor that detects traveling resistance.

35. The irradiation apparatus as defined in claim 28, wherein the radiation-source transport container or a transport module includes, as a component of the irradiation apparatus, electronic means for identifying the radiation source and for identifying characterizing variables of the storage drum.

* * * * *

UNITED STATES PATENT AND TRADEMARK OFFICE
CERTIFICATE OF CORRECTION

PATENT NO. : 6,137,114
DATED : October 24, 2000
INVENTOR(S) : Karl-Heinz Rohe, Johann Kindlein, Karl Weinlich, Wolfgang Schreckenberg It is certified that error appears in the above-identified patent and that said Letters Patent is hereby corrected as shown below:

Title page,

Item [73], change "Assignees: Isotopen-Technik; Dr. Sauerwein GmbH, both of Haan, Germany" to --Assignee:Isotopen-Technik Dr. Sauerwein GmbH, Haan, Germany--.

Signed and Sealed this

Twenty-second Day of May, 2001

Attest:

NICHOLAS P. GODICI

Attesting Officer

Acting Director of the United States Patent and Trademark Office